(12) United States Patent
Ondrus et al.

(10) Patent No.: US 9,790,148 B2
(45) Date of Patent: Oct. 17, 2017

(54) PROCESS FOR PRODUCING HIGHLY PURE CHLORINATED ALKANE

(71) Applicant: SPOLEK PRO CHEMICKOU A HUTNI VYROBU A.S., Utsi nad Labem (CZ)

(72) Inventors: Zdenek Ondrus, Vrbice (CZ); Pavel Kubicek, Decin (CZ); Karel Filas, Usti nad Labem (CZ); Petr Sladek, Usti nad Labem-Strekov (CZ)

(73) Assignee: SPOLEK PRO CHEMICKOU A HUTNI VYROBU A.S., Usti nad Labem (CZ)

( * ) Notice: Subject to any disclaimer, the term of this patent is extended or adjusted under 35 U.S.C. 154(b) by 0 days.

(21) Appl. No.: 14/883,646

(22) Filed: Oct. 15, 2015

(65) Prior Publication Data

US 2016/0107958 A1    Apr. 21, 2016

(30) Foreign Application Priority Data

Oct. 16, 2014  (CZ) ..................................... 2014-705

(51) Int. Cl.

| C07C 17/04 | (2006.01) |
| C07C 17/25 | (2006.01) |
| C07C 17/38 | (2006.01) |
| B01D 3/32 | (2006.01) |
| C07C 17/383 | (2006.01) |
| C07C 19/01 | (2006.01) |

(52) U.S. Cl.
CPC ............... *C07C 17/25* (2013.01); *B01D 3/32* (2013.01); *C07C 17/04* (2013.01); *C07C 17/38* (2013.01); *C07C 17/383* (2013.01); *C07C 19/01* (2013.01); *Y02P 20/582* (2015.11)

(58) Field of Classification Search
CPC ............................. C07C 17/04; C07C 17/354
See application file for complete search history.

(56) References Cited

U.S. PATENT DOCUMENTS

| 5,315,052 A * | 5/1994 | Taylor ..................... C07C 17/04 570/247 |
| 8,115,038 B2 * | 2/2012 | Wilson .................... C07C 17/10 570/227 |
| 2010/0331583 A1 | 12/2010 | Johnson et al. |
| 2012/0157723 A1 | 6/2012 | Fukuju et al. |
| 2014/0171698 A1 | 6/2014 | Elsheikh et al. |

(Continued)

FOREIGN PATENT DOCUMENTS

| EP | 1418345.3 | 5/2015 |
| WO | WO-2009/085862 | 7/2009 |

(Continued)

*Primary Examiner* — Medhanit Bahta
(74) *Attorney, Agent, or Firm* — Pearl Cohen Zedek Latzer Baratz LLP (57) ABSTRACT

Disclosed is a process for producing highly pure chlorinated alkane in which a chlorinated alkene is contacted with chlorine in a reaction zone to produce a reaction mixture containing the chlorinated alkane and the chlorinated alkene, and extracting a portion of the reaction mixture from the reaction zone, wherein the molar ratio of chlorinated alkane: chlorinated alkene in the reaction mixture extracted from the reaction zone does not exceed 95:5.

59 Claims, 3 Drawing Sheets

(56) References Cited

U.S. PATENT DOCUMENTS

2014/0228601 A1* 8/2014 Dawkins ................. C07C 17/38
                                                            570/230
2014/0235903 A1   8/2014 Wang et al.
2016/0096786 A1*  4/2016 Yang ....................... C07C 17/04
                                                            570/246

FOREIGN PATENT DOCUMENTS

| WO | WO-2012/098420 | 7/2012 | | |
|----|----------------|--------|---|---|
| WO | WO-2013/015068 | 1/2013 | | |
| WO | WO 2013022806 A1 * | 2/2013 | ............. | C07C 17/04 |
| WO | WO-2013/055894 | 4/2013 | | |
| WO | WO-2013/074324 | 5/2013 | | |
| WO | WO-2013/086262 | 6/2013 | | |
| WO | WO-2013/119919 | 8/2013 | | |
| WO | WO-2014/130445 | 8/2014 | | |

* cited by examiner

PROCESS FOR PRODUCING HIGHLY PURE CHLORINATED ALKANE

CROSS-REFERENCE TO RELATED APPLICATIONS

This application claims priority of Czech Patent Application No. PV 2014-705, filed Oct. 16, 2014, which is hereby incorporated by reference.

The present invention relates to processes for producing very high purity chlorinated alkane compounds, such as 1,1,1,2,3-pentachloropropane, 1,1,2,2,3-pentachloropropane, 1,1,1,3,3-pentachloropropane, 1,1,1,2,3,3-hexachloropropane, 1,1,1,2,3,3,3-heptachloropropane, 1,1,1,2,2,3,3-heptachloropropane and 1,1,1,2,2,3,3,3-octachloropropane and 1,1,1,2,4,4,4-heptachlorobutane and also to compositions comprising such compounds.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated, and in some cases, embraced in a number of applications, especially as refrigerants in the automotive and domestic fields. Examples of such compounds include 1,1,1,2-tetrafluoroethane (R-134a), 2-chloro-3,3,3-trifluoropropene (HFO-1233xf), 1,3,3,3-tetrafluoropropene (HFO-1234ze), 3,3,3-trifluoropropene (HFO-1243zf), and 2,3,3,3-tetrafluoropropene (HFO-1234yf), 1,2,3,3,3-pentafluoropropene (HFO-1225ye), 1-chloro-3,3,3-trifluoropropene (HFO-1233zd), 3,3,4,4,4-pentafluorobutene (HFO-1345zf), 1,1,1,4,4,4-hexafluorobutene (HFO-1336mzz), 3,3,4,4,5,5,5-heptafluoropentene (HFO1447fz), 2,4,4,4-tetrafluorobut-1-ene (HFO1354mfy) and 1,1,1,4,4,5,5,5-octafluoropentene (HFO-1438mzz)

While these compounds are, relatively speaking, chemically non-complex, their synthesis on an industrial scale to the required levels of purity is challenging. Many synthetic routes proposed for such compounds increasingly use, as starting materials or intermediates, chlorinated alkanes or alkenes. Examples of such processes are disclosed in WO2012/098420, WO2013/015068 and US2014/171698. The conversion of the chlorinated alkane or alkene starting materials to the fluorinated target compounds is usually achieved using hydrogen fluoride and optionally transition metal catalysts, for example chromium-based catalysts.

An example of an optionally non-catalytic process for preparing fluoroalkenes is disclosed in WO2013/074324.

The issue of the formation of impurities during hydrofluorination reactions is considered in US2010/331583 and WO2013/119919, where thus the need for part fluorinated feedstock purity is described, and also in US2014/235903 regarding reactor impurities.

It has been recognised that when the chlorinated feedstock is obtained from a multi-step process, especially if such steps are linked and run continuously to achieve industrially acceptable product volumes, then the need to prevent cumulative side reactions from generating unacceptable impurities at each process step is very important.

The purity of the chlorinated starting materials will have a substantial effect on the success and viability of the processes (especially continuous processes) for preparing the desirable fluorinated products. The presence of certain impurities will result in side reactions, minimising the yield of the target compound. Removal of these impurities through the use of distillation steps is also challenging. Additionally, the presence of certain impurities will compromise catalyst life, by, for example, acting as catalyst poisons.

Accordingly, there is a need for high purity chlorinated alkanes for use in the synthesis of the fluorinated compounds mentioned above. Several processes for producing purified chlorinated compounds have been proposed in the art.

For example, WO2013/086262 discloses a process for preparing 1,1,2,2,3-pentachloropropane from methylacetylene gas. As can be seen from the examples in that application, the bench scale syntheses disclosed therein resulted in a product having around 98.5% purity, despite being subjected to post-synthetic purification process steps, specifically distillation.

In WO2014/130445, a conventional process is discussed on page 2 of that publication, the first step of which involves the formation of 1,1,1,2,3-pentachloropropane from 1,1,3-trichloropropene. However, the purity profile of that intermediate product is not outlined, nor is any importance attached to the purity profile of that product. In Example 2 of WO2014/130445, a 240 db (1,1,1,2,3-pentachloropropane) rich material having a purity level of 96.5 to 98.5% is used.

WO2013/055894 discloses a process for producing tetrachloropropenes, particularly 1,1,2,3-tetrachloropropene and reports that the product obtained from the processes disclosed in that document have advantageously low levels of impurities which can be problematic in downstream processes for producing fluorocarbons. A discussion of the different types of impurities considered to be problematic by the authors of WO2013/055894 is set out in paragraphs [0016] and [0017] of that document US2012/157723 discloses a process in for preparing chlorinated alkanes via a three step process. Seemingly high purity chloroalkanes appear to have been prepared according to the process disclosed in that document. However, the purity data presented in the examples of that application are only given to one decimal place.

From the provision of data presented in this way, it is apparent that the analytical equipment used to measure the impurity profile of the products obtained in the examples of US2012/157723 was insensitive; conventional analytical apparatus enables hydrocarbon levels to 1 ppm (i.e. to four decimal places). Given that one skilled in the art would need to know the impurity profile of chloroalkane feedstocks to be used in industrial scale down to a ppm level, the data presented in US2012/157723 would not be of assistance.

The skilled person would also recognise that the process disclosed in US2012/157723 provides 1,1,1,2,3-pentachloropropane which has relatively low selectivity; as can be seen, from paragraph [0146] of that document, selectivity towards the compound of interest was 95%.

Additional processes in which processes are streamlined by using crude intermediates in downstream stages are disclosed in WO2009/085862.

Despite these advances, problems can still arise through the use of chlorinated compounds obtained from the processes discussed above. Particularly, the presence of impurities especially those which are not easily separable from the compounds of interest (e.g. as a result of similar or higher boiling points) or which reduce the effectiveness or operating life of catalysts used in downstream processes can be problematic.

To minimise such drawbacks, a demand remains for very high purity chlorinated alkane compounds, and also for efficient, selective and reliable processes for preparing such compounds, especially enabling continuous industrial manufacture.

Thus, according to a first aspect of the present invention, there is provided a process for producing highly pure chlorinated alkane in which a chlorinated alkene is contacted with chlorine in a reaction zone to produce a reaction mixture containing the chlorinated alkene and the chlorinated alkane and extracting a portion of the reaction mixture from the reaction zone, wherein the molar ratio of chlorinated alkane:chlorinated alkene in the reaction mixture extracted from the reaction zone does not exceed 95:5.

The molar ratio of chlorinated alkane:chlorinated alkene in the reaction mixture is controlled within numerically defined limits. As those skilled in the art will appreciate, in such embodiments, while control over the process is characterised herein in terms of the molar ratio between the chlorinated alkane starting material and the chlorinated alkene product, it can also considered as control over the conversion of starting material to product—thus a molar ratio of chlorinated alkane:chlorinated alkene of 95:5 equates to a conversion of 95%. The inventors have found that limiting the conversion of the starting material as outlined above minimises the formation of undesirable impurities. Additionally, where reference is made to a molar ratio of the starting material:product being greater than a given value, this means a greater degree of conversion of the starting material to product, i.e. such that the proportion of the product is increased while the proportion of the starting material is decreased.

In embodiments of the invention, the reaction zone may be a primary reaction zone.

The processes of the present invention involve the chlorination of an already chlorinated alkene to convert to the chlorinated alkane compound of interest. The process is highly selective.

One of the advantages of the processes of the present invention is that they permit the production of a target chlorinated alkane with high isomeric selectivity. Thus, in embodiments of the invention, the chlorinated alkane product is produced with isomeric selectivity of at least about 95%, at least about 97%, at least about 98%, at least about 99%, at least about 99.5%, at least about 99.7%, at least about 99.8% or at least about 99.9%.

It has been found that such highly pure chlorinated alkane materials are less susceptible to degradation during storage and transport. It is believed that this is due to the absence (or presence in only trace amounts) of impurities which would otherwise trigger decomposition of the chlorinated alkane of interest. Accordingly, the use of stabilising agents can advantageously be avoided.

A further advantage of the processes of the present invention is that, through control of the degree of conversion of the starting material to finished product, the formation of otherwise problematic serial products is minimised. Accordingly, in embodiments of the invention, reaction mixture extracted from the primary reaction zone, and/or chlorinated alkane rich material extracted from the principal reaction zone, comprises low levels of serial reaction products, i.e. compounds comprising a greater number of chlorine and/or carbon atoms than the chlorinated alkane product, for example in amounts of less than about 5%, less than about 2%, less than about 1%, less than about 0.5%, less than about 0.2%, less than about 0.1%, less than about 0.05% or less than about 0.02%.

In embodiments of the invention, the process may be continuous.

It has unexpectedly been found that through the careful control of the level of chlorinated alkane in the reaction mixture formed in the primary reaction zone, the production of impurities is minimised, and/or high selectivity for the desired chlorinated alkane, is achieved. The level of chlorinated alkane in the reaction mixture may be controlled by, for example, i) removing the chlorinated alkane (either specifically, or by extracting reaction mixture) from the primary reaction zone/s, ii) by controlling the reaction conditions in the primary reaction zone (e.g. temperature, exposure to light, and/or pressure), and/or iii) by controlling the amount of chlorinated alkene and/or chlorine present in the primary reaction zone.

For example, the amount of chlorine present in the reaction mixture can be controlled such that there is no molar excess of chlorine present in the reaction mixture in the primary and/or principal reaction zone/s Any conditions which result in the formation of the chlorinated alkane may be employed in the primary reaction zone. However, in embodiments of the invention, the operating temperature in the primary reaction zone is maintained at a relatively low level, for example about 100° C. or lower, about 90° C. or lower or about 80° C. or lower. The operating temperature of the primary reaction zone may be about −30° C., about −20° C., about −10° C. or about 0° C. to about 20° C., about 40° C., or about 75° C.

The use of such temperatures in the primary reaction zone has been found unexpectedly to be advantageous as this results in a reduction in the formation of isomers of the target chlorinated alkane and over-chlorinated compounds, yet gives the required product selectively in high yield. To increase the reaction rate at these temperatures, light (visible and/or ultra violet) may optionally be used to promote the addition of chlorine at these low temperatures.

The operating temperature in the primary reaction zone may be controlled by any temperature control means known to those skilled in the art, for example heating/cooling jackets, heating/cooling loops either internal or external to the reactor, heat exchangers and the like. Additionally or alternatively, the temperature may be controlled by controlling the temperature of material/s added into the reaction mixture, thus, controlling the temperature of the reaction mixture. The reaction mixture is maintained in the primary reaction zone for a time and under conditions sufficient to achieve the required level of chlorinated alkane in the reaction mixture.

In embodiments of the invention, the primary reaction zone may be exposed to light, for example visible light and/or ultra violet light. Exposure of the reaction mixture to light promotes the reaction when operated at low temperatures which is advantageous where the use of higher temperatures is to be avoided.

For the avoidance of doubt, in embodiments of the invention, the primary conversion step may be carried out in a plurality of primary reaction zones (e.g. 1, 2, 3, 4, 5, 6, 7, 8, 9, 10 or more primary reaction zones), which may be operated at the same or different pressures, temperatures and/or light conditions.

In embodiments of the present invention, the residence time of the reaction mixture in the primary reaction zone may range from about 30 to 300 minutes, from about 40 to about 120 minutes or from about 60 to about 90 minutes.

Optimal results have been observed when the level of chlorinated alkane in the reaction mixture present in the primary reaction zone is maintained at a level such that the molar ratio of chlorinated alkane:chlorinated alkene in reaction mixture extracted from the primary reaction zone does not exceed 50:50. In embodiments of the invention, the level of chlorinated alkane present in the reaction mixture in the primary reaction zone may be maintained at lower levels, for example such that the molar ratio of chlorinated alkane:chlorinated alkene in reaction mixture extracted from the primary reaction zone does not exceed 75:25, 50:50, 40:60 or 30:70. Additionally or alternatively, the level of chlorinated alkane in the reaction mixture present in the primary reaction zone/s is maintained at a level such that the molar ratio of chlorinated alkane:chlorinated alkene in reaction mixture extracted from the primary reaction zone is at least 5:95, 10:90, 15:85, 20:80, 30:70, 40:60 or 50:50.

The composition of reaction mixture, enabling a determination of the molar ratio of chlorinated alkane:chlorinated alkene, may be determined as soon as is practicable following extraction of the reaction mixture from the primary reaction zone. For example, a sample of reaction mixture may be extracted at a point adjacent to or slightly downstream of the outlet of the primary reaction zone. In embodiments of the invention, the outlet may be located at the upper end of the primary reaction zone.

Reaction mixture comprising chlorinated alkene starting material and chlorinated alkane product may be extracted from the primary and/or principal reaction zone either continuously or intermittently. One skilled in the art would recognise that, in embodiments where reaction mixture/chloroalkane rich product is extracted from the respective reaction zone, that material may be removed on a substantially continuous basis while the zone in question is at operating conditions and, if its purpose is to set up a steady state reaction (e.g. an chlorination), once the reaction mixture therein has attained the required steady state.

In embodiments of the present invention, the reaction conducted in the primary reaction zone is in the liquid phase, i.e., the reaction mixture present therein is predominantly or totally liquid. The reaction mixture may be analysed using any techniques known to those skilled in the art e.g. chromatography.

The chlorinated alkene employed in the processes of the present invention may be fed into the primary reaction zone using any technique known to those skilled in the art. The chlorinated alkene may be a $C_{2-6}$ chloroalkene, for example, chloroethene, chloropropene or chlorobutene, or a $C_{3-6}$ chloroalkene. Examples of chlorinated alkenes which may be employed in the processes of the present invention include 1,1,3-trichloropropene, 1,1,2-trichloropropene, 2,3,3-trichloropropene, 1,1,4,4,4-pentachlorobutene, 3,3,3-trichloropropene, 1,2,3-trichloropropene, 1,3-dichloropropene, 2-chloropropene, 1,1-dichloropropene, 1,1,2,3-tetrachloropropene, 1,1,3,3-tetrachloropropene, 1,1,2,3,3-pentachloropropene, 1,1,3,3,3-pentachloropropene and 1,1,2,3,3,3-hexachloropropene.

Chlorinated butenes, pentenes or hexenes may be employed in the processes of the present invention to produce chlorinated $C_{4-6}$ compounds which find utility in the production of fluorinated compounds having low global warming potential.

The chlorinated alkene used as a starting material in the processes of the present invention preferably has a high degree of purity. In embodiments of the invention, the chlorinated alkene has a purity level of at least about 95%, at least about 97%, at least about 99%, or at least about 99.5%.

Additionally or alternatively, the chlorinated alkene may include less than about 2%, less than about 1%, less than about 0.1%, less than about 0.01% or less than about 0.001% by weight of chlorinated alkene and/or chlorinated alkane impurities. For example, where the chlorinated alkene starting material is 1,1,3-trichloropropene, the 1,1,3-trichloropropene starting material may comprise less than about 2%, less than about 1%, less than about 0.1%, less than about 0.01% or less than about 0.001% by weight of chlorinated alkene impurities such as perchlorethylene, tetrachloroethylene, hexachloroethylene and/or chlorinated alkane impurities such as 1,1,1,3-tetrachloropropane.

Processes for producing high purity chlorinated alkene are disclosed in UK Patent Application No. 1418345.3 and Czech Patent Application No. PV 2014-706, the contents of which are incorporated herein by reference. Products of those processes may advantageously comprise:

about 95% or more, about 97% or more, about 99% or more, about 99.2% or more about 99.5% or more or about 99.7% or more of the chlorinated alkene, less than about 1000 ppm, less than about 500 ppm, less than about 200 ppm, or less than about 100 ppm of chlorinated $C_{5-6}$ alkane impurities, less than about 1000 ppm, less than about 500 ppm, less than about 200 ppm, or less than about 100 ppm of chlorinated alkene impurities (i.e. chlorinated alkenes other than the starting material), less than about 500 ppm, less than about 200 ppm, less than about 100 ppm, less than about 50 ppm, less than about 20 ppm, less than about 10 ppm or less than about 5 ppm metal (e.g. iron), less than about 1000 ppm, less than about 500 ppm, less than about 250 ppm, or less than about 100 ppm of oxygenated organic compounds, and/or less than about 500 ppm, about 250 ppm or less, about 100 ppm or less or about 50 ppm or less of water.

For the avoidance, the limits of metal outlined above encompass metal in elemental form (e.g. particulate metal) as well as in ionic form (e.g. in the form of a salt).

The chlorinated alkene material used as a starting material in the processes of the present invention may be provided in a composition having the impurity profile as outlined above.

The chlorinated alkane produced in the processes of the invention may be a $C_{2-6}$ chloroalkane, for example, chloroethane, chloropropane or chlorobutane, or a $C_{3-6}$ chloroalkane. Examples of chlorinated alkanes which may be produced in the processes of the invention include 1,1,1,2,3-pentachloropropane, 1,1,2,3-tetrachloropropane, 1,1,2,2,3-pentachloropropane, 1,1,1,2,2-pentachloropropane, 1,1,1,2,4,4,4-heptachlorobutane, 1,1,1,2,3,3-hexachloropropane, 1,1,1,2,3,3,3-heptachloropropane, 1,1,1,2,2,3,3-heptachloropropane and 1,1,1,2,2,3,3,3-octachloropropane.

The feed of chlorine and/or chlorinated alkene into the primary reaction zone/s and/or principal reaction zone/s employed in processes of the present invention may be continuous or intermittent.

Chlorine may be fed into reaction zone/s employed in the processes of the present invention in liquid and/or gaseous form, either continuously or intermittently. For example, the primary reaction zone may be fed with one or more chlorine feeds. Additionally or alternatively, reaction zone/s downstream of the primary reaction zone (e.g. the principal conversion zone) may be fed with one or more chlorine feeds. In embodiments of the invention, the only reaction zone supplied with chlorine is the primary reaction zone.

Where the reaction mixture in the reaction zone/s is liquid, the chlorine may be fed into the reaction zone/s as gas and dissolved in the reaction zone. In embodiments, the chlorine is fed into reaction zone/s via dispersing devices, for example, nozzles, porous plates, tubes, ejectors, etc. The chlorine, in embodiments of the invention, may be fed directly into the liquid reaction mixture. Additionally or alternatively, the chlorine may be fed into liquid feeds of other reactants upstream of the reaction zone/s.

Additional vigorous stirring may be used to ensure good mixing and/or dissolution of the chlorine into the liquid reaction mixture.

The chlorine used as a starting material in the processes of the present invention is preferably highly pure. In embodiments of the invention, the chlorine fed into the reaction zone/s employed at any stage in the present invention preferably has a purity of at least about 95%, at least about 97%, at least about 99%, at least about 99.5%, or at least about 99.9%

Additionally or alternatively, the chlorine used in the processes of the present invention may comprise bromine or bromide in an amount of about 200 ppm or less, about 100 ppm or less, about 50 ppm or less, about 20 ppm or less or about 10 ppm or less.

The use of chlorine gas comprising low amounts of oxygen (e.g. about 200 ppm or less, about 100 ppm or less, about 50 ppm or less, about 20 ppm or less or about 10 ppm or less) is also envisaged. However, in embodiments of the present invention, lower grade chlorine (including higher oxygen levels, e.g. of 1000 ppm or higher) can advantageously be employed without the final product of the processes of the present invention comprising unacceptably high levels of oxygenated impurities.

As mentioned above, it is envisaged that in embodiments of the invention, the reaction mixture present in the primary reaction zone will be liquid. However, alternative embodiments are envisaged in which the reaction mixture is gaseous. In such embodiments, the primary reaction zone may be operated at temperatures of about 150° C. to about 200° C. Gas phase reactors, for example, one or more tubular gas phase reactors, may be employed in such embodiments.

The term 'highly pure' as used herein means about 95% or higher purity, about 99.5% or higher purity, about 99.7% purity, about 99.8% or higher purity, about 99.9% or higher purity, or about 99.95% or higher purity. Unless otherwise specified, values presented herein as percentages are by weight.

Extraction of the reaction mixture from the primary reaction zone can be achieved using any technique known to those skilled in the art. Typically, reaction mixture extracted from the primary reaction zone will comprise unreacted chlorinated alkene, unreacted chlorine and chlorinated alkane. Alternatively, where control of the formation of chlorinated alkane is achieved by controlling (i.e. limiting) the amount of chlorine fed into the primary reaction zone, the reaction mixture extracted from the primary reaction zone may comprise very low levels of chlorine, for example about 1% or less, about 0.5% or less, about 0.1% or less, about 0.05% or less or about 0.01% or less.

In embodiments of the invention, where reaction mixture comprising unreacted chlorinated alkene is extracted from the primary reaction zone, a principal conversion step may be performed in which majority significant proportion, but not all, of the unreacted chlorinated alkene present in the reaction mixture extracted from the primary reaction zone is converted to chlorinated alkane, thus producing a chlorinated alkane rich product, which is then extracted from the principal reaction zone. The chlorinated alkane rich product may comprise unreacted chlorinated alkene starting material and chlorinated alkane product.

In such embodiments, the reaction mixture may additionally comprise chlorine. Additionally or alternatively, chlorine may be fed into the principal reaction zone to enable the chlorination reaction to proceed.

The degree of conversion of the chlorinated alkene to chlorinated alkane is controlled such that the molar ratio of chlorinated alkane:chlorinated alkene present in the chlorinated alkane rich product extracted from the principal reaction zone does not exceed about 95:5, about 93:7, about 91:9, about 90:10 or about 87.5:12.5.

Additionally or alternatively, the degree of conversion of the chlorinated alkene to chlorinated alkane is controlled such that the molar ratio of chlorinated alkane:chlorinated alkene present in the chlorinated alkane rich product extracted from the principal reaction zone is greater than about 70:30, about 75:25, about 80:20 or about 85:15.

In certain embodiments of the present invention in which a principal reaction step is carried out, the molar ratio of chlorinated alkane:chlorinated alkene present in the chlorinated alkane rich product extracted from the principal reaction zone is greater than that for reaction mixture extracted from the primary reaction zone. In other words, the degree of conversion of the starting material to product is higher for the product extracted from the principal reaction zone than for the reaction mixture extracted from the primary reaction zone.

In embodiments of the invention in which a chlorinated alkane rich product is employed or produced, it may have the chlorinated alkane:chlorinated alkene ratios outlined above.

It has unexpectedly been found that through the careful control of the degree of conversion of the chlorinated alkene in the principal reaction zone, the production of impurities is minimised. The level of chlorinated alkane in the reaction mixture may be controlled by, for example, i) removing the chlorinated alkane (either specifically, or by extracting chlorinated alkane rich product) from the principal reaction zone, ii) by controlling the reaction conditions in the principal reaction zone (e.g. temperature, exposure to light, and/or pressure), and/or iii) by controlling the amount of chlorinated alkene and/or chlorine present in the principal reaction zone.

In embodiments of the invention in which the degree of conversion of the chlorinated alkene to the chlorinated alkane is controlled (i.e. limited) by controlling the amount of chlorine present in the principal reaction zone (e.g. supplied directly thereto and/or present as a component of the reaction mixture), the chlorine content in the obtained chlorinated alkane rich product may be very low, for example about 1% or less, about 0.5% or less, about 0.1% or less, about 0.05% or less or about 0.01% or less.

This principal conversion step will typically take place in one or more principal reaction zones downstream of the primary reaction zone. Any number of principal reaction zones may be employed in the processes of the present invention, for example 1, 2, 3, 4, 5, 6, 7, 8, 9, 10 or more principal reaction zones.

Any conditions which result in the conversion of chlorinated alkene to chlorinated alkane may be employed in the principal conversion step. In embodiments of the invention, the principal conversion step may comprise a reduced temperature conversion step. When such a step is performed, the reduction in temperature of the extracted reaction mixture is preferably achieved by feeding the reaction mixture into a principal reaction zone operated at a reduced temperature (for example about −30 to about 30° C., about −25 to about 10° C., or more preferably about −20 to about −10° C.) and extracting a chlorinated alkane rich product from the principal conversion zone.

It has been unexpectedly found that maintaining, at low temperature, a reaction mixture comprising chlorinated alkene, chlorine and chlorinated alkane, results in the conversion of chlorinated alkene to chlorinated alkane while minimising the production of unwanted impurities, improving selectivity and/or the yield.

Thus, according to a further aspect of the invention, there is provided a process for producing highly pure chlorinated alkane comprising a reduced temperature conversion step in which a reaction mixture comprising chlorinated alkene, and chlorinated alkane is fed into a principal reaction zone, operated at a temperature of about −30° C. to about 30° C., about −25° C. to about 10° C., or more preferably about −20° C. to about −10° C., and extracting a chlorinated alkane rich product from the principal reaction zone.

For certain embodiments, exposure of the reaction mixture in the principal reaction zone to light (for example ultra violet light) is useful in conducting the reaction successfully at low temperatures.

In aspects of the invention, the ratio of chlorinated alkane:chlorinated alkene present in the reaction mixture fed in to the principal reaction zone may be 70:30 or lower, 60:40 or lower, 50:50 or lower, 40:60 or lower or 30:70 or lower and/or 5:95 or higher, 10:90 or higher, 20:80 or higher or 40:60 or higher.

In embodiments of the invention, the operating temperature of the principal reaction zone may be achieved in a single cooling action, or a series of cooling actions in which the principal reaction zone/s are operated at successively lower temperatures. Operating the principal reaction zone/s at reduced temperature can be achieved using any technique known to those skilled in the art.

The reduced temperature conversion step preferably takes place in one or more principal reaction zones downstream of the primary reaction zone. For example, where the reduced temperature conversion step requires a single cooling action, it may occur in a single principal reaction zone. Where the reduced temperature conversion step requires a series of cooling actions, this may be achieved in a single principal reaction zone, or in a plurality of principal reaction zones.

In embodiments of the present invention, the reaction mixture is maintained in the principal reaction zone for a time and under conditions sufficient to achieve the required level of chlorinated alkane in the reaction mixture.

The principal reaction zone/s may be operated under subatmospheric, atmospheric or superatmospheric pressure.

Additionally or alternatively, the primary and/or the principal reaction zone/s may be exposed to light, for example visible light and/or ultra violet light.

In embodiments of the present invention, the residence time of the reaction mixture in the principal reaction zone may range from about 30 to 300 minutes, from about 40 to about 120 minutes or from about 60 to about 90 minutes.

In embodiments of the present invention, the reaction conducted in the principal reaction zone is in the liquid phase, i.e, the reaction mixture present therein is predominantly or totally liquid.

In embodiments of the invention, reaction mixture extracted from the primary reaction zone is subjected directly to the principal conversion step. In alternative embodiments, the extracted reaction mixture is subjected to one or more pre-treatment steps prior to being subjected to the principal conversion step.

In embodiments of the invention, to attain the desired level of chlorinated alkane in the chlorinated alkane rich product, the principal conversion step may involve heating the chlorinated alkane rich product to elevated temperatures, for example to about 20° C. or higher, about 30° C. or higher, about 40° C. or higher, about 50° C. or higher or about 60° C. or higher.

Heating the chlorinated alkane rich product in this way may be achieved in a single heating step. Alternatively, the chlorinated alkane rich product may be subjected to a series of heating steps at successively higher temperatures.

As mentioned above, different reaction zones may be operated at different temperatures, pressure and/or to the exposure to differing types and/or intensity of light. For example, reaction mixture extracted from the primary reaction zone/s could be passed into a first principal reaction zone in which a reduced temperature conversion step is carried out. The obtained chlorinated alkane rich product could then be passed into a second principal reaction zone downstream of the first principal reaction zone in which a heat treatment or UV exposure step is performed, to convert the bulk of the remaining unreacted chlorinated alkene present to the chlorinated alkane product. Alternatively, the reduced-temperature conversion step and heating and/or UV exposure steps could all take place in the principal reaction zone.

Thus, in embodiments of the invention, a plurality of principal reaction zones may be employed in sequence. For ease of comprehension, these may be characterised as upstream principal reaction zones and downstream principal reaction zones, the upstream principal reaction zones being upstream of the downstream principal reaction zones when those zones are operated in sequence.

In such embodiments, there may be any number of upstream principal reaction zones and/or downstream principal reaction zones, for example 1, 2, 3, 4, 5, 6, 7, 8, 9 or 10 or more upstream principal reaction zones and/or downstream principal reaction zones.

Where such arrangements are employed, heat treatment and/or light (e.g. ultraviolet light) exposure may be conducted in some or all of the upstream and/or downstream principal reaction zones. The intensity of the light exposure may be higher in the downstream principal reaction zones. Additionally or alternatively, the wavelength of the light to which the reaction mixture is exposed in the downstream principal reaction zones may be lower than that in the upstream principal reaction zones.

In certain embodiments of the invention, heat treatment and/or light exposure steps may only be conducted in the downstream principal reaction zones.

One advantage of the processes of the present invention is that desirous results are obtained whether the primary and/or principal reaction zones are operated in a continuous or batch process. The terms 'continuous process' and 'batch process' will be understood by those skilled in the art.

Any type of reactor known to those skilled in the art may be employed in the processes of the present invention. Specific examples of reactors that may be used to provide primary reaction zone/s and/or principal reaction zone/s are column reactors (e.g. column gas-liquid reactors), tubular reactors (e.g. tubular gas phase reactors), bubble column reactions, plug/flow reactors and stirred tank reactors, for example continuously stirred tank reactors.

Reactors used in the present invention may be divided into different zones each having different flow patterns and/or different operating temperatures/pressures. For example, the principal conversion step may be performed in a reactor including a plurality of principal reaction zones. Those zones may be operated at different temperatures and/or pressures. For example, in embodiments where the principal conversion step is a reduced temperature conversion step, the principal reaction zones may be operated at successively lower temperatures.

Additionally or alternatively, reactors used in the processes of the present invention may be provided with external circulation loops. The external circulation loops may optionally be provided with cooling and/or heating means.

As those skilled in the art will recognise, reaction zones can be maintained at differing temperatures through use of cooling/heating elements such as cooling tubes, cooling jackets, cooling spirals, heat exchangers, heating fans, heating jackets or the like.

Some or all of the primary and/or principal reaction zones used in the processes of the present invention may be exposed to visible light (natural or artificially generated), ultra violet light and/or be operated in darkness.

Chlorine, either in liquid, in solution, and/or gaseous form, may be fed into the principal reaction zone/s. Chlorinated alkene may also or alternatively be fed into the principal reaction zone/s, if required.

Those skilled in art will recognise that, in certain embodiments, the reaction zones utilised at any stage in the processes of the present invention may require agitation means, e.g. stirrers, followers, flow channeling means or the like and the use of such means in the primary and/or principal reaction zones in the processes of the present invention is envisaged. The primary and/or principal reaction zones may be operated with differing flow types of reaction mixture.

The primary and/or principal reaction zones employed in the processes of the present invention may be located within a single or multiple reactors. Thus, for example, in embodiments of the invention, all of the primary reaction zones could be different reaction zones in a single reactor, for example, a column liquid-gas reactor.

Alternatively, the primary reaction zones could be in different reactors (e.g. a series of continuously stirred tank reactors) or even different types of reactors (e.g. one or more primary reaction zones could be in a continuously stirred tank reactor and additional primary reaction zone/s could be in a tube reactor).

It has unexpectedly been found that the formation of chlorinated alkane degradation products can be minimised if the apparatus employed to operate the processes of the present invention (or at least those parts of it which come into contact with the reaction mixture and/or product streams) does not comprise certain materials.

Thus according to a further aspect of the present invention, there is provided a process for producing a highly pure chlorinated alkane from a chlorinated alkene starting material wherein the apparatus for conducting the process is configured such that those parts of the apparatus which come into contact with the chlorinated alkane product and/or the chlorinated alkene, in use of the apparatus, comprise less than about 20%, about 10%, about 5%, about 2% or about 1% of iron.

In such embodiments of the present invention, the apparatus for conducting the process is configured such that those parts of the apparatus which come into contact with the chlorinated alkane product and/or the chlorinated alkene are produced from fluoropolymers, fluorochloropolymers, glass, enamel, phenolic resin impregnated graphite, silicium carbide and/or fluoropolymer impregnated graphite. The combination of glass, PVDF, ETFE and Hastelloy, may be used for achieving a combination of effects, for example to provide the necessary conditions for visible or ultraviolet light to be provided to the reaction mixture while also ensuring that other problems such as corrosion and temperature are controlled.

In embodiments of the invention, the principal reaction zone is in a plug/flow reactor. An advantage of the use of such apparatus is that the reactor can be configured to minimise or prevent back flow mixing.

The process steps outlined above minimise the formation of impurities, especially those impurities which are difficult to remove from the target chlorinated alkane product.

To maximise the purity of the reaction mixture extracted from the primary reaction zone or the chlorinated alkane rich product obtained from the principal reaction zone, additional purification steps may be carried out. For example, one or more distillation steps may be conducted. Such distillation steps may be conducted under low temperature/reduced pressure conditions.

Additionally or alternatively, one or more hydrolysis steps may be performed. In embodiments in which the reaction mixture/chlorinated alkane rich product (either typically being a mixture comprising the chlorinated alkene, the chlorinated alkane and impurities including oxygenated organic compounds) is subjected to a hydrolysis step, this typically involves contacting the reaction mixture extracted from the primary reaction zone/chlorinated alkane rich product with an aqueous medium in a hydrolysis zone. Examples of aqueous media which may be employed in the hydrolysis step include water, steam and aqueous acid.

Hydrolysis is conducted at appropriate conditions to allow hydrolysis reaction(s), if any, to proceed.

Performance of a hydrolysis step is preferable as this reduces the content of oxygenated organic compounds present in the reaction mixture/chlorinated alkane rich product. Examples of oxygenated organic compounds include chlorinated alkanols, chlorinated acid chlorides, chlorinated acids, or chlorinated ketones.

In embodiments of the invention in which a hydrolysis step is performed, the reaction mixture/chlorinated alkane rich product subjected to such a step may have an oxygenated organic compound content of about 500 ppm or less, about 200 ppm or less, about 100 ppm or less, about 50 ppm or less, or about 10 ppm or less.

Thus, according to a further aspect of the present invention, there is provided a process for removing oxygenated organic compounds from a chlorinated alkane rich product (obtainable from any upstream process) comprising a chlorinated alkane, a chlorinated alkene and oxygenated organic compounds, comprising feeding the chlorinated alkane rich product into an aqueous treatment zone, contacting the chlorinated alkane rich product with an aqueous medium to produce a mixture and extracting i) an organic phase from that mixture or ii) a chlorinated alkane stream from that mixture, the organic phase/chlorinated alkane stream comprising reduced levels of oxygenated organic compounds as compared to the chlorinated alkane rich product fed into the aqueous treatment zone.

In processes of the present invention in which a hydrolysis step is performed, the reaction mixture/chlorinated alkane rich product fed into the aqueous treatment zone may have a low chlorine content, for example about 0.8% or less, about 0.5% or less, about 0.1% or less, about 0.05% or less or about 0.01% or less. For the avoidance of doubt, where reference is made in this context to chlorine, this encompasses free chlorine, unreacted chlorine, and dissolved chlorine. Chlorine which is bonded to atoms other than chlorine should not be considered.

In embodiments of the invention, the hydrolysis zone is in a washing tank. In such embodiments, the reaction mixture/chlorinated alkane rich product may be washed with water and/or steam.

Once the reaction mixture/chlorinated alkane rich product has been contacted with the aqueous medium to form a mixture in the hydrolysis zone, that mixture may be subjected to one or more treatment steps. For example, components of reaction mixture/chlorinated alkane rich product (e.g. the chlorinated alkane product and/or unreacted chlorinated alkene starting material) can be extracted from the mixture formed in the aqueous treatment zone, for example via distillation preferably under reduced pressure and/or low temperature. Such a step can be achieved while the mixture is present in the aqueous treatment zone. Additionally or alternatively, the mixture may firstly be extracted from the aqueous treatment zone and subjected to the extraction step remotely from that zone.

Additionally or alternatively, in embodiments of the invention, a biphasic mixture may be formed in the aqueous treatment zone. In such embodiments, a phase separation step may be performed in which the organic phase comprising at least the chlorinated alkane component of the reaction mixture/chlorinated alkane rich product is separated from the aqueous waste phase. This may be achieved by the sequential extraction of the phases from the aqueous treatment zone. Alternatively, the biphasic mixture could be extracted from the aqueous treatment zone and subjected to a phase separation step remote from the aqueous treatment zone to extract the organic phase.

The organic phase may, after optional filtering may then be subjected to distillation to obtain streams comprising purified chlorinated alkane product and/or unreacted chlorinated alkene starting material. The chlorinated alkene starting material may be recycled to the primary and/or principal reaction zone/s.

Additionally or alternatively, the organic phase can be subjected to additional hydrolysis steps as outlined above. The hydrolysis steps can be repeated if required, for example, one, two, three or more times.

In embodiments of the invention, mixtures comprising the chlorinated alkane of interest (e.g. the reaction mixture obtained from the primary reaction zone, the chlorinated alkane rich product obtained from the principal reaction zone, the mixture formed in the aqueous treatment zone and/or the organic phase extracted from the biphasic mixture) can be subjected to a distillation step, preferably conducted at a temperature of about 100° C. or lower, about 90° C. or lower or about 80° C. or lower.

Such a distillation step may be conducted under vacuum. Where vacuum distillation is carried out, the vacuum conditions may be selected such that the distillation may be conducted at a low temperature and/or to facilitate the extraction of higher molecular weight chlorinated alkanes.

In embodiments of the invention, any distillation steps conducted in the process of the present invention may result in streams comprising at least about 50%, at least about 80%, at least about 90%, at least about 95%, at least about 97%, at least about 98%, at least about 99%, at least about 99.5%, at least about 99.7%, at least about 99.8%, or at least about 99.9% of i) unreacted chlorinated alkene starting material and/or ii) chlorinated alkane product being obtained. As used herein, the term 'streams' should be construed broadly to encompass a composition obtained from any distillation step, regardless of the apparatus used or the form of the composition obtained.

Any distillation equipment known to those skilled in the art can be employed in the processes of the present invention, for example a distillation boiler/column arrangement. However, it has unexpectedly been found that the formation of chlorinated alkane degradation products can be minimised if distillation apparatus formed of certain materials are avoided.

Thus according to a further aspect of the present invention, there is provided a method of distilling a chlorinated alkane rich product (regardless of the process from which it was obtained), in which distillation apparatus is employed, the distillation apparatus being free of components which, in use of the distillation apparatus, would come into contact with the process fluids (including the liquid or distillate) and comprise about 20% or more, about 10% or more, about 5% or more, about 2% or more or about 1% or more of iron.

In embodiments of the invention in which distillation step/s are carried out, the distillation apparatus may be configured such that all of its components which, in use of the distillation apparatus, would come into contact with the distillate or process fluid, are produced from fluoropolymers, fluorochloropolymers, glass, enamel, phenolic resin impregnated graphite, silicium carbide and/or fluoropolymer impregnated graphite.

Where distillation steps are performed as part of the processes of the present invention, streams obtained in such steps which comprise the chlorinated alkene starting material employed in the processes of the invention may be recycled and fed into the primary and/or principal reaction zone/s.

The processes of the present invention are particularly advantageous as they enable highly pure chlorinated alkanes to be produced using simple and straightforward techniques and equipment with which one skilled in the art would be familiar.

As can be seen from the disclosure provided herein, the inventive processes of the present invention can be operated in an integrated process in a fully continuous mode, optionally in combination with other processes. The process steps of the present invention may employ starting compounds which are converted to highly pure intermediates which are themselves further processed to the required target chlorinated compounds. Those compounds have the requisite purity to be employed as feedstocks in a range of downstream processes, for example hydrofluorination conversions.

In embodiments of the invention, the processes of the invention can be used to produce high purity chlorinated alkane compositions which comprise:

The chlorinated alkane product in amounts of at least about 95%, at least about 99.5%, at least about 99.7%, at least about 99.8%, at least about 99.9%, or at least about 99.95%, and one or more of the following:

Oxygenated organic compounds in amounts of less than about 500 ppm, about 250 ppm or less, about 100 ppm or less, about 50 ppm or less, or about 10 ppm or less, Isomers of the chlorinated alkane of interest in amounts of less than about 500 ppm or less, about 250 ppm or less, or about 100 ppm or less, Non-isomeric alkane impurities in amounts of less than about 500 ppm, about 250 ppm or less, or about 100 ppm or less, Chlorinated alkenes in amounts of less than about 500 ppm, about 250 ppm or less, about 100 ppm or less, or about 50 ppm or less, Water in amounts of less than about 500 ppm, about 250 ppm or less, about 100 ppm or less, or about 50 ppm or less, Inorganic compounds of chlorine in amounts of about 100 ppm or less, about 50 ppm or less, about 20 ppm or less, or about 10 ppm or less, Brominated organic compounds in amounts of about 100 ppm or less, about 50 ppm or less, about 20 ppm or less, or about 10 ppm or less, and/or Iron, in amounts of less than about 500 ppm, less than about 200 ppm, less than about 100 ppm, less than about 50 ppm, less than about 20 ppm, less than about 10 ppm or less than about 5 ppm.

For the avoidance of doubt, the term 'inorganic compounds of chlorine' encompasses non-organic compounds containing chlorine, including chlorine ($Cl_2$), hydrogen chloride and phosgene.

In embodiments of the present invention, the composition may comprise less than about 1000 ppm, less than about 500 ppm, less than about 200 ppm, or less than about 100 ppm of organic compounds other than the chlorinated alkane of interest. Additionally or alternatively, the composition may collectively comprise less than about 0.5%, less than about 0.3%, less than about 0.1% of organic compounds other than the chlorinated alkane of interest.

In embodiments in which the chlorinated alkane product is 1,1,1,2,3-pentachloropropane, the process of the invention can be used to produce a high purity composition which comprises:

1,1,1,2,3-pentachloropropane in amounts of at least about 99.6%, at least about 99.7%, at least about 99.8%, at least about 99.9%, or at least about 99.95%, Oxygenated organic compounds, including chlorinated propionyl chloride, chlorinated propanol and chlorinated propionic acid in amounts of about 1000 ppm or less, about 500 ppm or less, about 100 ppm or less, about 50 ppm or less, or about 10 ppm or less of all three compounds, Chlorinated propane isomers other than 1,1,1,2,3-pentachloropropane in amounts of 1000 ppm or less, about 500 ppm or less, about 250 ppm or less, or about 100 ppm or less, Chlorinated propenes in amounts of 1000 ppm or less, about 500 ppm or less, about 250 ppm or less, about 100 ppm or less, or about 50 ppm or less, Water in amounts of about 500 ppm or less, about 250 ppm or less, or about 100 ppm or less, Brominated organic compounds in amounts of about 100 ppm or less, about 50 ppm or less, about 20 ppm or less, or about 10 ppm or less Inorganic compounds of chlorine in amounts of about 100 ppm or less, about 50 ppm or less, about 20 ppm or less or about 10 ppm or less and/or Iron in amounts of about 100 ppm or less, about 50 ppm or less, about 20 ppm or less, about 10 ppm or less or about 5 ppm or less.

In embodiments of the present invention in which the chlorinated alkane product is 1,1,1,2,3-pentachloropropane, the composition may comprise less than about 1000 ppm, less than about 500 ppm, less than about 200 ppm, or less than about 100 ppm of organic compounds other than 1,1,1,2,3-pentachloropropane. Additionally or alternatively, the composition may comprise less than about 1000 ppm, less than about 500 ppm, less than about 200 ppm, or less than about 100 ppm of 1,1,3,3-Tetrachloropropene, 1,1,1,2,3,3-Hexachloropropane, and/or 1,1,1,2,2,3-Hexachloropropane.

As mentioned previously, the prior art fails to disclose or teach processes for producing chlorinated alkanes having such a high degree of purity and in high yield, with selective reaction. Thus, according to further aspects of the present invention, there are provided high purity chlorinated alkane compositions as set out above.

Additionally, the compositions as outlined above have impurity profiles which make them especially well suited to use as starting materials in the synthesis of fluoroalkanes or fluoroalkenes and/or chlorofluorinated alkenes. Thus, according to a further aspect of the present invention, there is provided the use of the compositions outlined herein as feedstocks in the synthesis of the above-identified fluoroalkanes/fluoroalkenes and/or chlorofluoroalkenes. In one embodiment of this aspect of the present invention, the compositions may be used to produce 2,3,3,3-tetrafluoropropene (HFO-1234yf)). In another embodiment of this aspect of the present invention, the compositions may be used to produce 2-chloro-3,3,3-trifluoropropene (HFO-1233xf).

The reaction zones employed at any stage in the processes of the present invention may be operated at differing pressures and/or temperatures and/or have differing flows (e.g. flows of differing intensity/direction) of reaction mixture therein.

The reaction zones employed at any stage in the processes of the present invention may be operated in sequence (e.g. where reaction mixture is passed from an initial upstream reaction zone to a terminal downstream reaction zone, optionally via intermediate reaction zones) and/or in parallel.

In embodiments where the reaction zones are operated in sequence and at differing temperatures and/or pressures, the temperature and/or pressure in some or all of the reaction zones may increase or decrease successively.

One, some or all of the reaction zones employed in the processes of the present invention may be operated at subatmospheric, atmospheric or superatmospheric pressure.

For the avoidance of doubt, where reference is made to units of pressure (kPa) it is the absolute value which is identified. Where values are presented as percentages, they are percentages by weight unless otherwise stated.

BRIEF DESCRIPTION OF DRAWINGS

| | |
|---|---|
| 1 | gaseous chlorine |
| 2 | column gas-liquid reactor |
| 3 | external circulation loop |
| 4 | external cooler |
| 5 | external circulation loop |
| 6 | 1,1,3-trichloropropene feed stream |
| 7 | external circulation loop |
| 8 | 1,1,1,2,3-pentachloropropane-rich stream |
| 9 | cooler |
| 10 | 1,1,1,2,3-pentachloropropane-rich stream (feed to hydrolysis step, FIG. 2) |
| 11 | off-gas |

| 101 | water stream |
| 102 | 1,1,1,2,3-pentachloropropane-rich feed stream |
| 103 | washing tank |
| 104 | washing tank outlet |
| 105 | filter |
| 106 | filter cake |
| 107 | 1,1,1,2,3-pentachloropropane-rich product stream |
| 108 | wastewater stream |

| 201 | 1,1,1,2,3-pentachloropropane-rich feed stream (product stream 107, FIG. 2) |
| 202 | distillation boiler |
| 203 | distillation residue stream |
| 204 | filter |
| 205 | filter cake |
| 206 | heavies stream |
| 207 | vacuum distillation column |
| 208 | distillate stream |
| 209 | condenser |
| 210 | intermediate line |
| 211 | liquid divider |
| 212 | reflux stream |
| 213.1 | 1,1,3-trichloropropene stream |
| 213.2 | 1,1,1,3-tetrachloropropane stream |
| 213.3 | purified 1,1,1,2,3-pentachloropropane stream |

EXAMPLES

Abbreviations used:
TCPe=1,1,3-trichloropropene
PCPa=1,1,1,2,3-pentachloropropane
HCE=hexachloroethane
DCPC=dichloropropanoylchloride The present invention is now further illustrated in the following example.

Example 1

Continuous Production of 1,1,1,2,3-pentachloropropane

Figure 1:
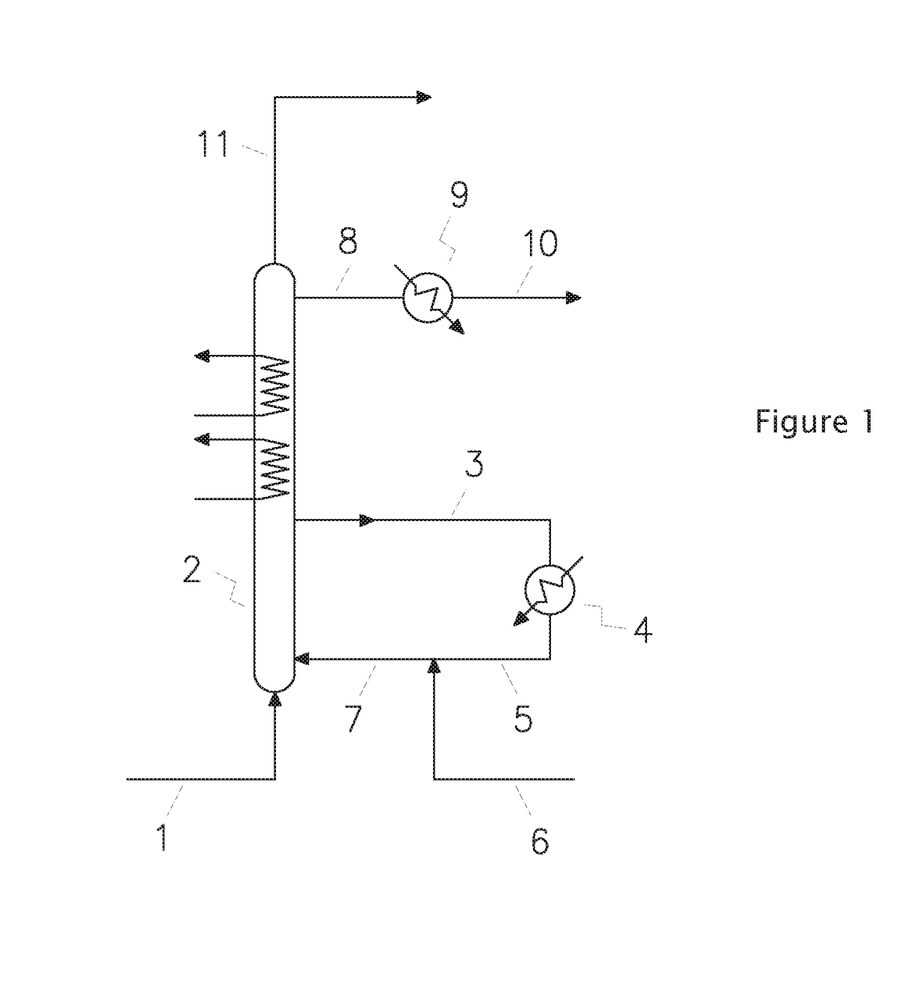
FIG. 1—Primary conversion and principal conversion steps (1,1,3-trichloropropene conversion to 1,1,1,2,3-pentachloropropane)

A schematic diagram of the equipment used to perform the primary conversion step and principal conversion step of the present invention is provided as FIG. 1. A liquid stream of 1,1,3-trichloropropene is fed via line 6 into an external circulation loop 3, 5, 7 connected to a column gas-liquid reactor 2. Gaseous chlorine is fed in the reactor 2 via line 1. The reactor 2 is includes a single primary reaction zone, namely circulation loop 3, 5, 7 and lower part of the reactor 2. The circulation loop 3, 5, 7 is provided with an external cooler 4 to control the temperature of the reaction mixture. Thorough mixing of 1,1,3-trichloropropene and chlorine is achieved within the primary reaction zone. The primary conversion step could equally be conducted in one or more other types of reactor, such as continuously stirred tank reactor/s.

The operating temperature within the primary reaction zone is 0° C. to 20° C. Operating the reactor within this range was found to minimise the formation of pentachloropropane isomers, which are difficult to separate from the target product, 1,1,1,2,3-pentachloropropane. Thorough mixing of the reaction mixture and mild temperatures, but also controlling the proportion of 1,1,1,2,3-pentachloropropane present in the reaction mixture, was found to minimise serial reactions of 1,1,3-trichloropropene and the formation of 1,1,1,3,3-pentachloropropane (which is difficult to separate from 1,1,1,2,3-pentachloropropane). To increase the rate of reaction at the low temperatures, the reaction mixture is exposed to visible light.

The reaction mixture is then passed up through the reactor 2 for the principal conversion step, which is performed as a reduced temperature conversion step. Cooling of the reaction mixture is achieved using cooling tubes, and the reaction mixture is passed through a series of upstream and downstream principal reaction zones (not shown), resulting in zonal chlorination of 1,1,3-trichloropropene. To drive the reaction towards completion, the reaction mixture in the downstream principal reaction zone is exposed to ultraviolet light. Advantageously, this fully utilizes the chlorine starting material such that the obtained reaction mixture which is extracted from the downstream-most principal reaction zone has very low levels of dissolved chlorine.

Operating the principal reaction zones at such temperatures has been found to minimise the serial reactions of 1,1,3-trichloropropene, which result in the formation of unwanted and problematic impurities, such as hexachloropropane.

A 1,1,1,2,3-pentachloropropane rich stream is extracted from reactor 2 via line 8. Off-gas is extracted from the reactor 2 via line 11. The 1,1,1,2,3-pentachloropropane rich stream is subjected to cooling using a product cooler 9 and passed via line 10 for a hydrolysis step. A schematic diagram illustrating the equipment used to conduct this step is presented as FIG. 2.

Figure 2:
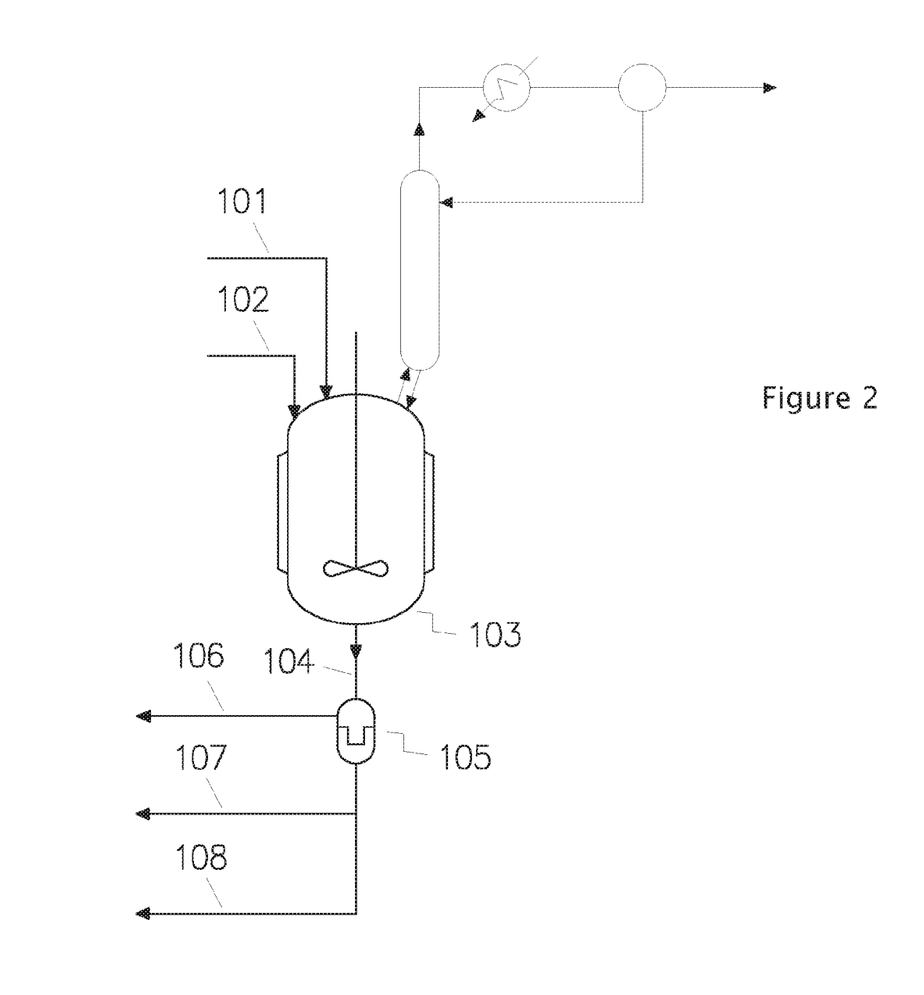
FIG. 2—Hydrolysis step

In that equipment, the 1,1,1,2,3-pentachloropropane rich stream is fed into washing tank 103 via line 102. Water is fed into the washing tank via line 101 to form a biphasic mixture. The organic phase (containing the 1,1,1,2,3-pentachloropropane rich product) can easily be separated from the aqueous phase by the sequential removal of those phases via line 104. The extracted phases are filtered 105 with the filter cake being removed 106. The 1,1,1,2,3-pentachloropropane rich product is then fed via line 107 for further processing while wastewater is removed via line 108.

The hydrolysis step is especially effective at removing oxygenated organic compounds, such as chlorinated propionyl chloride and their corresponding acids and alcohols, which may be formed during the processes of the present invention. While the formation of such compounds can be avoided by excluding the presence of oxygen from the upstream stages of the synthesis, doing so increases the cost of production. Thus, the hydrolysis step assists with the economic and straightforward removal of such otherwise problematic (owing to the difficulty of removing them, e.g. by distillation) impurities.

Figure 3:
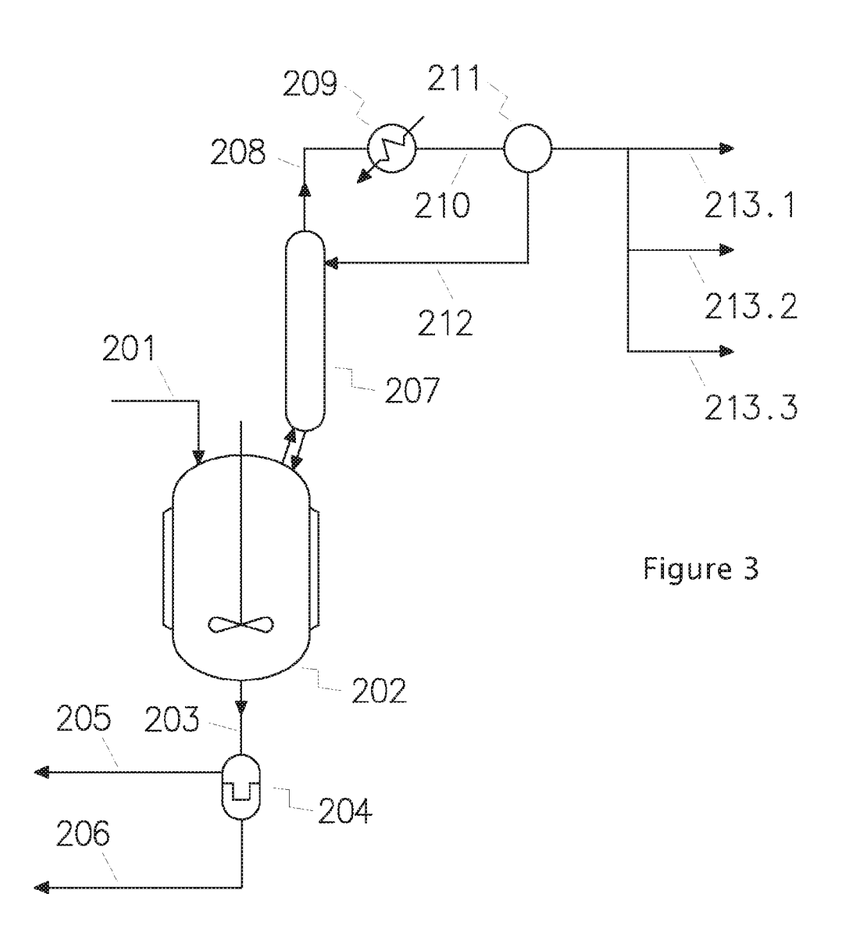
FIG. 3—Distillation step

To maximise the purity of the obtained 1,1,1,2,3-pentachloropropane, a vacuum distillation step was performed, using the apparatus shown in FIG. 3, namely a distillation boiler 202 and vacuum distillation column 207. Advantageously, the components of the distillation apparatus which come into contact with the process liquid and distillate are formed of non-metallic materials which prevents the formation of degradation products of the 1,1,1,2,3-pentachloropropane.

The vacuum distillation column 207 is provided with a liquid side stream withdrawal which can be used to prevent contamination of the product stream with light molecular weight compounds which may be formed in the boiler.

The 1,1,1,2,3-pentachloropropane rich product from the apparatus shown in FIG. 2 is fed into boiler 202 via line 201. A residue is extracted from the distillation boiler 202 via line 203, subjected to filtering using a filter 204. The filter cake is extracted from the system 205 and a heavies stream is extracted via line 206 and subjected to further processing.

Distillate is taken from the distillation column 201 via line 208, fed via condenser 209, intermediate line 210 and liquid divider 211 to yield a streams of i) 1,1,3-trichloropropene via line 213.1 which is recycled to the primary reaction zone, ii) 1,1,1,3-tetrachloropropane via line 213.2 and purified 1,1,1,2,3-pentachloropropane via line 213.3. A reflux stream 212 from divider 211 is fed back into the vacuum distillation column 207.

Using the apparatus and process conditions outlined above, 3062 kg of 1,1,3-Trichloropropene (113TCPe, purity 97.577%) was continuously processed with an average hourly loading 44.9 kg/h to produce 1,1,1,2,3-Pentachloropropane (11123PCPa). Basic parameters of the process are as follows:

| Basic parameters | |
|---|---|
| Reactor overall mean residence time (min) | 375 |
| Reactor temperature range (° C.) | 1-30 |
| Reactor pressure (kPa) | 101 |
| Overall reaction 113TCPe conversion (%) | 91.3 |
| Overall 11123PCPa reaction yield (mol PCPa/mol TCPe converted, in %) | 97.9 |
| Overall 11123PCPa yield including the all process steps described in Example 1 | 97.4 |

The full impurity profile of the purified product obtained in line 213.3. in FIG. 3 of the above-described embodiment is presented in the following table:

| Compound | (% wt) |
|---|---|
| Phosgene | ND |
| 1,1,3-Trichloroprop-1-ene | 0.007 |
| 2,3-Dichloropropanoylchloride | ND |
| 1,2.3-Trichloropropane | ND |
| 2,3,3,3-Tetrachloroprop-1-ene | 0.001 |
| 1,1,3,3-Tetrachloroprop-1-ene | 0.003 |
| 1,1,1,3-Tetrachloropropane | 0.002 |
| 1,2,3-Tetrachloroprop-1-ene | 0.003 |
| 1,1,3,3,3-Pentachloroprop-1-ene | 0.001 |
| 1,1,1,3-Pentachloropropane | 0.004 |
| hexachloroethane | ND |
| 2,3-Dichloropropanoicacid | ND |
| 1,1,1,2,3-Pentachloropropane | 99.967 |
| 1,1,2,2,3-Pentachloropropane | 0.001 |
| 1,1,1,3-Tetrachlororopropane-2-ol | 0.001 |
| 1-Bromo-1,1,2,3-Tetrachloropropane | ND |
| 2-Bromo-1,1,1,3-Tetrachloropropane | ND |
| 1,1,1,3,3,3-Hexhachloropropane | ND |
| 1,1,1,2,3,3-Hexachloropropane | 0.002 |
| 1,1,1,2,2,3-Hexachloropropane | 0.001 |
| 1,2-Dibromo-1,1,3-Trichloropropane | ND |
| HCl as Cl— | ND |
| $H_2O$ | 0.005 |

ND means below 0.001% wt.

Example 2

Ultra Pure Composition 1,1,1,2,3-pentachloropropane (PCPA)

The process of Example 1 was repeated four times and samples of 1,1,1,2,3-pentachloropropane were obtained following distillation using the apparatus illustrated in FIG. 3. Distillation was conducted at a pressure of around 15 mBar and at a maximum boiler temperature of 105° C. As can be seen in the following table, the process of the present invention enables highly pure PCPA, including very low levels of impurities, particularly 1,1,2,2,3-pentachloropropane which is very difficult to separate from 1,1,1,2,3-pentachloropropane using distillation. Note that the figures in this table are provided as percentages by weight of the composition.

| | Trial Number | | | |
|---|---|---|---|---|
| Compound | 2-1 | 2-2 | 2-3 | 2-4 |
| Phosgene | ND | ND | ND | ND |
| 1,1,3-Trichloroprop-1-ene | 0.0014 | 0.0012 | 0.0006 | 0.0014 |
| 2,3-Dichloropropanoyl chloride | ND | ND | ND | ND |
| 1,2.3-Trichloropropane | ND | ND | ND | ND |
| 2,3,3,3-Tetrachloroprop-1-ene | 0.0005 | 0.0002 | <0.0001 | 0.0002 |
| 1,1,3,3-Tetrachloroprop-1-ene | 0.0017 | 0.0021 | 0.0008 | 0.0015 |
| 1,1,1,3-Tetrachloropropane | 0.0023 | 0.0013 | 0.0007 | 0.0013 |
| 1,1,2,3-Tetrachloroprop-1-ene | 0.0018 | 0.0021 | 0.0008 | 0.0011 |
| 1,1,3,3,3-Pentachloroprop-1-ene | ND | ND | ND | ND |
| 1,1,1,3,3-Pentachloropropane | 0.002 | 0.0022 | 0.0009 | 0.0016 |
| hexachloroethane | ND | ND | ND | <0.0001 |
| 2,3-Dichloropropanoic acid | ND | ND | ND | ND |
| 1,1,1,2,3-Pentachloropropane | 99.984 | 99.985 | 99.993 | 99.989 |
| 1,1,2,2,3-Pentachloropropane | 0.0006 | 0.0009 | 0.0008 | 0.0009 |
| 1,1,1,3-Tetrachlororopropane-2-ol | 0.001 | 0.0008 | 0.0006 | 0.0005 |
| 1-Bromo-1,1,2,3-Tetrachloropropane | ND | ND | ND | ND |
| 2-Bromo-1,1,1,3-Tetrachloropropane | ND | ND | ND | ND |
| 1,1,1,3,3,3-Hexachloropropane | ND | ND | ND | ND |
| 1,1,1,2,3,3-Hexachloropropane | 0.0006 | 0.0004 | ND | 0.0005 |
| 1,1,1,2,2,3-Hexachloropropane | ND | 0.0003 | ND | ND |
| 1,2-Dibromo-1,1,3-Trichloropropane | ND | ND | ND | ND |
| Moisture (mg/kg) | 44 | 23 | NP | NP |
| Iron (mg/kg) | <0.05 | 0.05 | NP | NP |
| HCl as Chlorides (mg/kg) | 0.51 | 0.53 | NP | NP |

ND = below 1 ppm,
NP = not performed

Example 3

Effect of Water Treatment

Crude 1,1,1,2,3-Pentachloropropane compositions were obtained using the apparatus depicted in FIG. 1 and described in Example 1 above, e.g. the compositions were obtained from line 10 in FIG. 1. One stream (Trial 3-1) was not subjected to a hydrolysis step, while the other was (Trial 3-2), using the apparatus shown in FIG. 2 and described in Example 1 above. The resulting crude compositions were then subjected to distillation. The purity of and oxygenated compound contents of the samples, pre- and post-distillation, are shown in the following table:

| Trial Number | 3-1 | 3-2 |
|---|---|---|
| Pre-distillation | | |
| 1,1,1,2,3-Pentachloropropane | 89.038 | 91.402 |
| Sum of oxygenated as propanoyl chlorides and their acids | 0.006 | 0.001 |
| Post-distillation | | |
| 1,1,1,2,3-Pentachloropropane | 99.948 | 99.930 |
| Sum of oxygenated as propanoyl chlorides and their acids | 0.006 | <0.001 |

As is apparent, the washing step can be successfully employed to minimise the content of oxygenated organic impurities in compositions rich in chlorinated alkanes of interest.

Example 4

Influence of Molar Ratio of Chorinated Alkene:Chlorinated Alkane on Impurity Formation A batch operated reactor consisting of a four neck glass flask equipped with a stirrer, thermometer, back cooler, feed and discharge neck and cooling bath was set up. The feedstock consisted of 1,1,3-Trichloropropene comprising perchloroethylene and oxygenated impurities in amounts observed in commercially sourced supplies.

Minor amounts of HCl gas were formed and these together with traces of chlorine were cooled down by means of a back cooler/condenser and then absorbed in a caustic soda scrubber. Chlorine was introduced into the liquid reaction mixture via dip pipe in various amounts for a period of 90 minutes. The temperature of reaction was maintained at 26 to 31° C. Pressure was atmospheric. The chlorine was totally consumed during the reaction. The reaction mixture was sampled and analyzed by GC and the results of this analysis are shown in the following table:

| Trial No. | 4-1 | 4-2 | 4-3 | 4-4 | 4-5 |
|---|---|---|---|---|---|
| chlorine dosed (mol % of stoichiometry) | 20% | 40% | 60% | 80% | 100% |
| TCPe:PCPa ratio in reaction mixture (mol %) | 90:10 | 72:28 | 53:47 | 33:67 | 14:86 |
| HCE (w %) | 0.015 | 0.025 | 0.040 | 0.064 | 0.099 |
| DCPC (w %) | 0.089 | 0.067 | 0.172 | 0.228 | 0.322 |
| Other oxygenated (w %) | | 0.009 | 0.017 | 0.030 | 0.058 |

As can be seen, increasing the conversion of the chlorinated alkene starting material to the chlorinated alkane product of interest results in an increase in the formation of impurities in the reaction mixture. These disadvantageous results arise as conversion of the starting material to product approaches total conversion.

Example 5

Influence of Molar Ratio of Chlorinated Alkene:Chlorinated Alkane on Isomeric Selectivity This example was carried out in as described in Example 4 above. 1,1,3-Trichloropropene (purity 94.6% containing 5% of 1,1,1,3-Tetrachloropropane as an impurity) was used as the feedstock.

4 trials at different reaction temperature were conducted. The samples of reaction mixture were taken at 80%, 90%, 95% and 100% of stoichiometric quantity of chlorine dosed (based on 113TCPe in the feedstock) and then analyzed by gas chromatography. The results of this analysis are shown in the following table:

| Chlorine dosed (mol % of 113TCPe in feedstock) | | 80% | 90% | 95% | 100% |
|---|---|---|---|---|---|
| Trial Nr. | Reaction temp. | 11133PCPA content in reaction mixture in % | | | |
| 5-1 | 6° C. | 0.028 | 0.040 | 0.053 | 0.075 |
| 5-2 | 25° C. | 0.040 | 0.055 | 0.071 | 0.099 |
| 5-3 | 45° C. | 0.049 | 0.064 | 0.076 | 0.095 |
| 5-4 | 63° C. | 0.056 | 0.071 | 0.086 | 0.112 |

These results demonstrate that increasing the conversion of the chlorinated alkene starting material to the chlorinated alkane product of interest results in a decrease in the selectivity of the reaction towards the chlorinated alkane isomer of interest.

These disadvantageous results arise as conversion of the starting material to product approaches total conversion.

Example 6

Influence of Molar Ratio of Chlorinated Alkene:Chlorinated Alkane on Impurity Formation This chlorination step was carried out as described in Example 4 above. 1,1,3-Trichloropropene (purity 99.4%) was used as a feedstock.

Chlorine was introduced into the liquid reaction mixture at 120% of the stoichiometric quantity towards feedstock 1,1,3-Trichloropropene for a period of 90 minutes and was totally consumed during the reaction. The reaction temperature was 80° C. and reactor pressure was atmospheric. The samples of reaction mixture were taken by 80%, 95%, 110% and 120% of stoichiometric quantity of the chlorine dosed was analyzed by gas chromatography. Reaction selectivity is expressed in the table below as a ratio between sum of major impurities (1,1,3,3-Tetrachloropropene, 1,1,1,2,3,3-Hexachloropropane, 1,1,1,2.2.3-Hexachloropropane) to the product 1,1,1,2,3-Pentachloropropane:

| Trial Number | 6-1 | 6-2 | 6-3 | 6-4 |
|---|---|---|---|---|
| chlorine dosed (mol % of stoichiometry) | 80 | 95 | 110 | 120 |
| TCPe:PCPa ratio in reaction mixture (mol %) | 22:78 | 11:89 | 0.6:99.4 | 0.2:99.8 |
| Sum of byproducts/ 11123PCPa (%) | 3.51 | 3.59 | 4.28 | 6.34 |

These results demonstrate that increasing the conversion of the chlorinated alkene starting material to the chlorinated alkane product of interest results in an increase in the formation of unwanted impurities. These disadvantageous results arise as conversion of the starting material to product approaches total conversion. As can be seen, the degree of conversion (and thus the formation of impurities) can advantageously and conveniently be achieved by controlling the amount of chlorine into the reaction zone, such that there is no molar excess of chlorine:chlorinated alkene starting material.

Example 7

Removal of Oxygenated Impurities by Hydrolysis

To demonstrate the effectiveness of the hydrolysis step of the present invention at removing oxygenated compounds from the chlorinated alkane product of interest, samples of crude reaction mixture reaction mixture were obtained using the apparatus depicted in FIG. 1 and described in Example 1 above, e.g. the composition was obtained from line 10 in FIG. 1. The content of a specific oxygenated compound known to be problematic in downstream reactions was analysed (Feed). The sample was then subjected to a hydrolysis step using the apparatus depicted in FIG. 2 and described above in Example 1, and the organic phase, e.g. the composition obtained from line 107 in FIG. 2 was analysed (After treatment). The results are shown in the following table:

| Trial Number | Content of specific oxygenated compound (ppm) | |
| --- | --- | --- |
| 7-1 | Feed | After treatment |
| 2,3-Dichloropropanoyl chloride | 937 | 23 |

As can be seen from this example there is about 97.5% efficiency in the removal of this specific oxygenated impurity.

The invention claimed is:

1. A process for producing highly pure chlorinated alkane in which a chlorinated alkene is fed into a reaction zone and contacted with chlorine in said reaction zone to produce a reaction mixture containing the chlorinated alkane and the chlorinated alkene, and extracting a portion of the reaction mixture from the reaction zone, wherein the molar ratio of chlorinated alkane:chlorinated alkene in the reaction mixture extracted from the reaction zone does not exceed 95:5.

2. The process of claim 1, wherein the chlorinated alkene is 1,1,3-trichloropropene and the chlorinated alkane is 1,1,1,2,3-pentachloropropane.

3. The process of claim 1, wherein the process is continuous.

4. The process of claim 1, wherein the reaction zone is a primary reaction zone.

5. The process of claim 4, wherein the molar ratio of chlorinated alkane:chlorinated alkene in the reaction mixture extracted from the primary reaction zone does not exceed 50:50.

6. The process of claim 4, wherein the operating temperature in the primary reaction zone is about −10° C. to about 50° C.

7. The process of claim 4, wherein the reaction mixture extracted from the primary reaction zone is subjected to a principal conversion step in a principal reaction zone to produce a chlorinated alkane rich product, which is extracted from the principal reaction zone.

8. The process of claim 7, wherein the molar ratio of chlorinated alkane:chlorinated alkene in both i) the reaction mixture extracted from the primary reaction zone and ii) the chlorinated alkane rich product extracted from the principal reaction zone does not exceed 95:5 and wherein the molar ratio of chlorinated alkane:chlorinated alkene in the chlorinated alkane rich product extracted from the principal reaction zone is higher than the molar ratio of chlorinated alkane:chlorinated alkene in the reaction mixture extracted from the primary reaction zone.

9. The process of claim 7, wherein the reaction mixture extracted from the primary reaction zone and/or the chlorinated alkane rich product extracted from the principal reaction zone has a chlorine level of about 1% or less.

10. The process of claim 7, wherein the principal conversion step comprises a reduced temperature conversion step in which the reaction mixture extracted from the primary reaction is fed into a principal reaction zone operated at a reduced temperature and the chlorinated alkane rich product is extracted from the principal reaction zone.

11. The process according to claim 7, wherein the primary and/or the principal reaction zone is exposed to visible light and/or ultraviolet light.

12. The process according to claim 7 wherein a plurality of principal reaction zones are employed in sequence and the reaction mixture in the downstream principal reaction zones is exposed to ultraviolet light and/or heating.

13. The process according to claim 12, wherein the reaction mixture in the downstream-most principal reaction zone is exposed to ultraviolet light and/or heating.

14. The process according to claim 7, wherein the level of chlorine present in the primary and/or principal reaction zone/s is controlled such that there is no molar excess of chlorine present in the reaction mixture present in the primary and/or principal reaction zone/s.

15. The process according to claim 1, wherein the reaction mixture is subjected to a hydrolysis step.

16. The process according to claim 15, wherein the hydrolysis step comprises contacting the reaction mixture with an aqueous medium in an aqueous treatment zone.

17. The process according to claim 16, wherein the aqueous medium forms a mixture with the reaction mixture, the process further comprising the step of extracting an organic phase from the mixture.

18. The process of claim 17 wherein the organic phase extracted from the mixture formed in the aqueous treatment zone comprises oxygenated organic compounds, said oxygenated organic compounds being present in amounts of about 1000 ppm or less.

19. The process of claim 16, wherein the reaction mixture fed into the aqueous treatment zone comprises less than about 0.1% chlorine.

20. The process of claim 15, wherein the reaction mixture is further subjected to one or more distillation steps.

21. The process of claim 20, wherein a distillation step is performed before and/or after the hydrolysis step.

22. The process of claim 21, wherein the distillation step is performed in a distillation column including a rectification section and a purified stream of the chlorinated alkane is extracted as a liquid phase side product from the rectification section of the distillation column.

23. The process according to claim 7, wherein the chlorinated alkane rich product is subjected to a hydrolysis step.

24. The process according to claim 23, wherein the hydrolysis step comprises contacting the chlorinated alkane rich product with an aqueous medium in an aqueous treatment zone.

25. The process according to claim 24, wherein the aqueous medium forms a mixture with the chlorinated alkane rich product, the process further comprising the step of extracting a chlorinated alkane stream from that mixture.

26. The process according to claim 25, wherein the chlorinated alkane stream extracted from the mixture formed in the aqueous treatment zone comprises oxygenated organic compounds in amounts of about 1000 ppm or less.

27. The process according to claim 24, wherein the chlorinated alkane rich product fed into the aqueous treatment zone comprises less than about 0.1% chlorine.

28. The process according to claim 7, wherein the chlorinated alkane rich product is further subjected to one or more distillation steps.

29. The process of claim 17, wherein the organic phase extracted from the mixture formed in the aqueous treatment zone is subjected to one or more distillation steps.

30. A process for producing highly pure chlorinated alkane in which a chlorinated alkene is contacted with chlorine in a primary reaction zone to produce a reaction mixture containing the chlorinated alkane and the chlorinated alkene, and extracting a portion of the reaction mixture from the primary reaction zone, wherein the molar ratio of chlorinated alkane:chlorinated alkene in the reaction mixture extracted from the primary reaction zone does not exceed 95:5, wherein the reaction mixture extracted from the primary reaction zone is subjected to a principal conversion step in a principal reaction zone to produce a chlorinated alkane rich product, which is extracted from the principal reaction zone, and wherein the principal conversion step comprises a reduced temperature conversion step in which the reaction mixture extracted from the primary reaction is fed into a principal reaction zone operated at a reduced temperature of about −30° C. to about 30° C., and the chlorinated alkane rich product is extracted from the principal reaction zone.

31. The process according to claim 30, wherein the primary and/or the principal reaction zone is exposed to visible light and/or ultraviolet light.

32. The process according to claim 30, wherein the level of chlorine present in the primary and/or principal reaction zone/s is controlled such that there is no molar excess of chlorine present in the reaction mixture present in the primary and/or principal reaction zone/s.

33. The process according to claim 30, wherein the chlorinated alkane rich product is subjected to a hydrolysis step.

34. The process according to claim 33, wherein the hydrolysis step comprises contacting the chlorinated alkane rich product with an aqueous medium in an aqueous treatment zone.

35. The process according to claim 34, wherein the aqueous medium forms a mixture with the chlorinated alkane rich product, the process further comprising the step of extracting a chlorinated alkane stream from that mixture.

36. The process according to claim 35, wherein the chlorinated alkane stream extracted from the mixture formed in the aqueous treatment zone comprises oxygenated organic compounds in amounts of about 1000 ppm or less.

37. The process according to claim 34, wherein the chlorinated alkane rich product fed into the aqueous treatment zone comprises less than about 0.1% chlorine.

38. The process according to claim 33, wherein the chlorinated alkane rich product is further subjected to one or more distillation steps.

39. The process according to claim 34, wherein the aqueous medium forms a mixture with the reaction mixture, the process further comprising the step of extracting an organic phase from the mixture, and wherein the organic phase extracted from the mixture formed in the aqueous treatment zone is subjected to one or more distillation steps.

40. A process for producing a product rich in a chlorinated alkane comprising a reduced temperature conversion step in which a reaction mixture comprising chlorine, chlorinated alkene and the chlorinated alkane is fed into a principal reaction zone operated at a temperature of about −30° C. to about 10° C., and extracting the product rich in the chlorinated alkane from the principal reaction zone.

41. The process according to claim 40, wherein the level of chlorine present in the principal reaction zone is controlled such that there is no molar excess of chlorine present in the reaction mixture present in the principal reaction zone.

42. A process for producing a product rich in a chlorinated alkane comprising a reduced temperature conversion step in which a reaction mixture comprising chlorine, chlorinated alkene and the chlorinated alkane is fed into a principal reaction zone operated at a temperature of about −30° C. to about 30° C., and extracting the product rich in the chlorinated alkane from the principal reaction zone.

43. The process according to claim 42, wherein the level of chlorine present in the principal reaction zone is controlled such that there is no molar excess of chlorine present in the reaction mixture present in the principal reaction zone.

44. A process for producing a product rich in a chlorinated alkane comprising a reduced temperature conversion step in which a reaction mixture comprising chlorine, chlorinated alkene and the chlorinated alkane is fed into a principal reaction zone operated at a temperature of about −30° C. to about 10° C., and extracting the product rich in the chlorinated alkane from the principal reaction zone, wherein the principal reaction zone is exposed to visible light and/or ultraviolet light.

45. A process for producing a product rich in a chlorinated alkane comprising a reduced temperature conversion step in which a reaction mixture comprising chlorine, chlorinated alkene and the chlorinated alkane is fed into a principal reaction zone operated at a temperature of about −30° C. to about 30° C., and extracting the product rich in the chlorinated alkane from the principal reaction zone, wherein the principal reaction zone is exposed to visible light and/or ultraviolet light.

46. A process for producing a product rich in a chlorinated alkane comprising a reduced temperature conversion step in which a reaction mixture comprising chlorine, chlorinated alkene and the chlorinated alkane is fed into a principal reaction zone operated at a temperature of about −30° C. to about 10° C., and extracting the product rich in the chlorinated alkane from the principal reaction zone, wherein the chlorinated alkane rich product is subjected to a hydrolysis step.

47. The process according to claim 46, wherein the hydrolysis step comprises contacting the chlorinated alkane rich product with an aqueous medium in an aqueous treatment zone.

48. The process according to claim 47, wherein the aqueous medium forms a mixture with the chlorinated alkane rich product, the process further comprising the step of extracting a chlorinated alkane stream from that mixture.

49. The process according to claim 48, wherein the chlorinated alkane stream extracted from the mixture formed in the aqueous treatment zone comprises oxygenated organic compounds in amounts of about 1000 ppm or less.

50. The process according to claim 47, wherein the chlorinated alkane rich product fed into the aqueous treatment zone comprises less than about 0.1% chlorine.

51. The process according to claim 46, wherein the chlorinated alkane rich product is further subjected to one or more distillation steps.

52. The process according to claim 47, wherein the aqueous medium forms a mixture with the reaction mixture, the process further comprising the step of extracting an organic phase from the mixture, and wherein the organic phase extracted from the mixture formed in the aqueous treatment zone is subjected to one or more distillation steps.

53. A process for producing a product rich in a chlorinated alkane comprising a reduced temperature conversion step in which a reaction mixture comprising chlorine, chlorinated alkene and the chlorinated alkane is fed into a principal reaction zone operated at a temperature of about −30° C. to about 30° C., and extracting the product rich in the chlorinated alkane from the principal reaction zone, wherein the chlorinated alkane rich product is subjected to a hydrolysis step.

54. The process according to claim 53, wherein the hydrolysis step comprises contacting the chlorinated alkane rich product with an aqueous medium in an aqueous treatment zone.

55. The process according to claim 54, wherein the aqueous medium forms a mixture with the chlorinated alkane rich product, the process further comprising the step of extracting a chlorinated alkane stream from that mixture.

56. The process according to claim 55, wherein the chlorinated alkane stream extracted from the mixture formed in the aqueous treatment zone comprises oxygenated organic compounds in amounts of about 1000 ppm or less.

57. The process according to claim 54, wherein the chlorinated alkane rich product fed into the aqueous treatment zone comprises less than about 0.1% chlorine.

58. The process according to claim 53, wherein the chlorinated alkane rich product is further subjected to one or more distillation steps.

59. The process according to claim 54, wherein the aqueous medium forms a mixture with the reaction mixture, the process further comprising the step of extracting an organic phase from the mixture, and wherein the organic phase extracted from the mixture formed in the aqueous treatment zone is subjected to one or more distillation steps.

* * * * *

UNITED STATES PATENT AND TRADEMARK OFFICE
CERTIFICATE OF CORRECTION

PATENT NO. : 9,790,148 B2
APPLICATION NO. : 14/883646
DATED : October 17, 2017
INVENTOR(S) : Zdenek Ondrus et al.

It is certified that error appears in the above-identified patent and that said Letters Patent is hereby corrected as shown below:

On the Title Page

Under Applicant data (71) please correct the Applicant's address to read:
Usti nad Labem (CZ)

Signed and Sealed this
Tenth Day of April, 2018

Andrei Iancu
*Director of the United States Patent and Trademark Office*